United States Patent [19]
Friedland

[11] 3,952,761
[45] Apr. 27, 1976

[54] SYSTEM FOR CONTROLLING DENSITY OF LIQUIDS

[76] Inventor: Donald Friedland, 3619 Bedford Ave., Brooklyn, N.Y. 11210

[22] Filed: Mar. 25, 1974

[21] Appl. No.: 454,667

[52] U.S. Cl. .................................. 137/91; 73/445; 73/452; 73/453
[51] Int. Cl.² .......................................... G01N 9/18
[58] Field of Search ............ 137/91, 4; 73/445, 451, 73/452, 453

[56] References Cited
UNITED STATES PATENTS

| | | | |
|---|---|---|---|
| 1,067,073 | 7/1913 | Steiger | 73/452 |
| 1,688,811 | 10/1928 | Henny | 73/445 |
| 1,838,845 | 12/1931 | Lanaux | 73/452 |
| 1,957,941 | 5/1934 | Coe | 73/452 |
| 2,362,661 | 11/1944 | Peters | 73/452 |
| 3,089,502 | 5/1963 | Davidson | 73/453 X |

FOREIGN PATENTS OR APPLICATIONS

| | | | |
|---|---|---|---|
| 40,991 | 10/1887 | Germany | 73/445 |
| 1,401,989 | 5/1965 | France | 73/453 |

*Primary Examiner*—Alan Cohan
*Attorney, Agent, or Firm*—Robert I. Pearlman

[57] ABSTRACT

A system for accurately controlling the density of liquids in a processing system employing a chamber having a finned hydrometer with control activation mechanism floating in a reservoir of continuous sample solution, and having a plurality of chambers so constructed as to create a liquid stream feeding the zone containing the hydrometer and imparting rotational motion thereto. The height of the hydrometer is sensed as measuring the density of the liquid sample. Appropriate corrections are made to the processing system.

7 Claims, 1 Drawing Figure

U.S. Patent   April 27, 1976   3,952,761
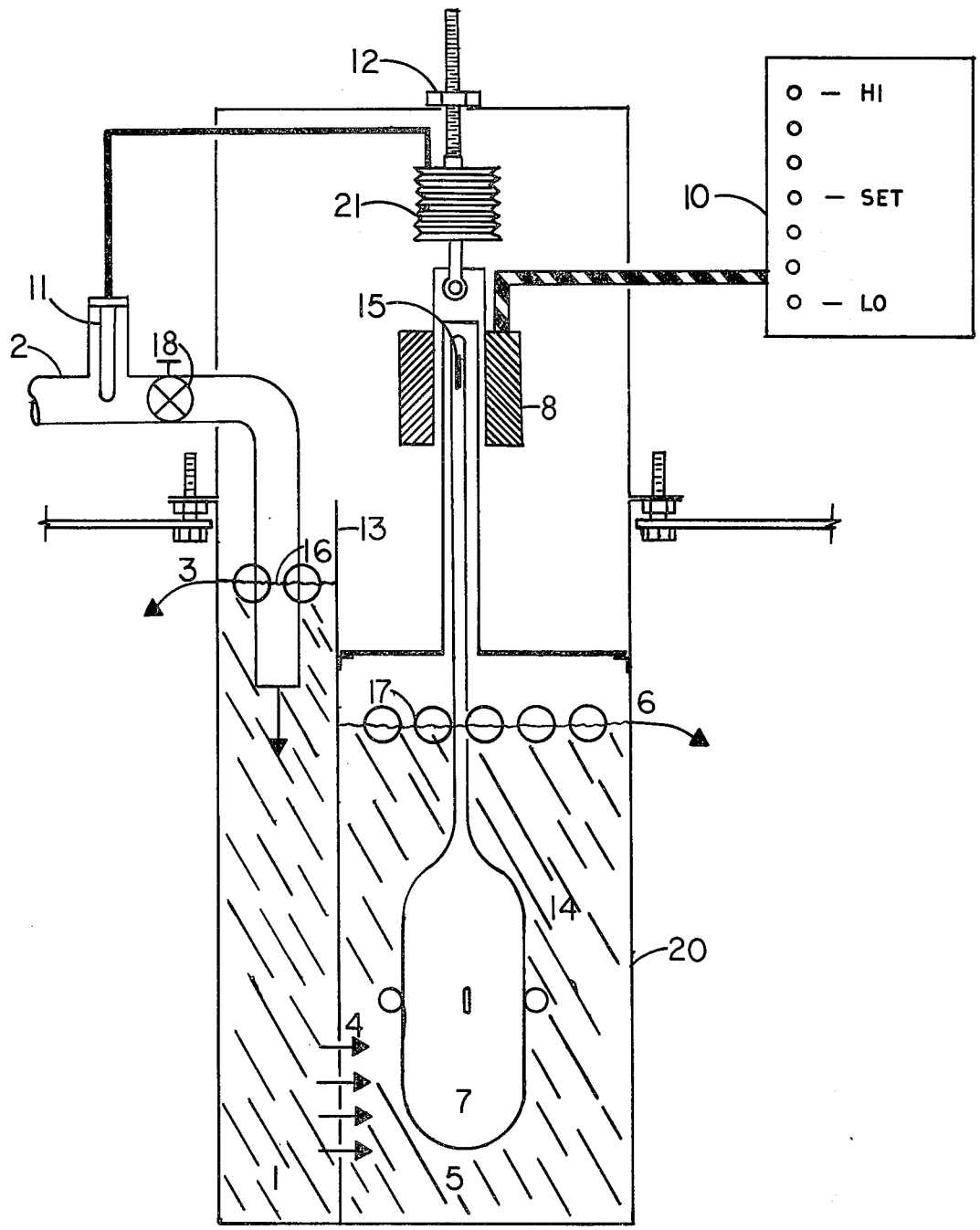

SYSTEM FOR CONTROLLING DENSITY OF LIQUIDS

BACKGROUND OF THE INVENTION

The present invention is concerned with a method and apparatus for accurately controlling various chemical and physical processes in which liquids are involved and in which it is desired to control the concentration and/or specific gravity of the liquids in the system. In such systems it is necessary to monitor variations in liquid compositions occasioned by the addition or removal of other liquids, concentration of dissolved constituents therein, etc. Typical of such operations are the manufacture of various beverages and liquid products, such as beer, soups, gasoline, milk and wine.

While it has been suggested in the past to use a hydrometer in a reservoir of sampled solution as a means of monitoring the operation of such processes, e.g. see U.S. Pat. No. 2,320,720, such systems have in general not found wide use due to the difficulty in obtaining accurate meaasurements and sensing small variations. The hydrometer itself often tends to stick in its position. Additionally, changes in flow rate, temperature and the like have not in the prior art systems been readily accommodated. Controlling accuracy within a very small degree has been unobtainable.

SUMMARY OF INVENTION

The present invention deals with a system whereby excellent monitoring of the concentration or density of liquids in a processing system is obtained, thereby affording effective means of varying process conditions to very accurately maintain desired concentrations, specific gravity, etc. More particularly, applicant employs a monitoring arrangement comprising a plurality of zones. Sampled liquid is fed into the first zone which is normally separated from the second zone by a baffle having openings in a portion of the area separating the two zones. The first zone serves as a stabilization area for receipt of the liquid to be sampled. The second zone contains a finned hydrometer and solution is fed thereto through said openings from the first zone. The feeding of the solution creates streams of liquid which cooperate with the fins on the hydrometer to ensure constant revolution thereof and therefore free movement of the hydrometer within the control head unaffected by friction and surface tension and therefore highly accurate readings. These readings in turn are used to monitor the operation of the process.

In a preferred embodiment, the hydrometer cooperates with a movable control head having means for sensing the height of the hydrometer above the liquid surface (and accordingly the density of the solution in which it is floating). The initial position of the control head may be fixed to correspond to the desired conditions of the liquid in the system being sampled so that changes in height of the hydrometer sensed by the control head serves to indicate the directional deviation of the sampled solution from the desired set condition. This, in turn, can be used to actuate valves, pumps, or the like for feeding or removing components to the processing unit, means for increasing heat or cooling thereto, and various other alternative means of changing processing conditions to return the circulating solutions to the desired gravity of concentration condition.

The various aspects and modifications of the present invention will be made more clearly apparent by reference to the following drawings and accompanying description.

The drawing illustrates the overall combination of features for monitoring the gravity of the liquid being sampled from the processing unit.

Referring in detail to the drawing shown therein is a control monitoring unit operating in accordance with the present invention. Not shown are the processing units which can be of various types such as is typically used for the manufacture of industrial solutions, beverages or the like, and which per se are not part of the present invention. Suffice it to note that a sample of the processing solution is withdrawn, normally continuously, from an appropriate point corresponding to that at which the solution density is to be monitored and fed by pipe 2 into the control monitor system. Typically, this is done continuously.

Control monitor 20 comprises basically chambers 1 and 5, with finned hydrometer 7 being positioned in the liquid reservoir formed in the second chamber 5. The two zones are typically formed by having a baffle wall 13 between them with the baffle wall having one or more openings or holes 4 which serves to allow liquid to flow from chamber 1 to chamber 5. A difference in liquid height 16 and 17 in the two chambers is maintained by appropriate positioning of overflow holes 3 and 6 for return of sample solution to the liquid processing system. Thus, liquid fed through pipe 2 is sufficient to raise the height of liquid in chamber 1 to level 16 at which time it is significantly higher than level 17 of the liquid in chamber 5. Some of the liquid in chamber 1 flows out through holes 3 back into the system while a flow is created into chamber 5 by means of holes 4 in baffle 13. In the same manner liquid is returned to the system by overflow holes 6 positioned in the upper portion of chamber 5.

While the drawing illustrates the use of an annular initial chamber for feeding the chamber containing the control hydrometer, it is obvious that other configurations can be used such as a central pipe concentrically surrounded by an outer chamber containing the finned hydrometer with appropriate means for imparting liquid stream flow from the initial stabilizing chamber to the monitoring chamber.

The initial chamber serves to stabilize conditions, eliminate bubbles, as well as providing a liquid stream flow for rotation of hydrometer 7 by means of its finned structure 14 thereby insuring that the latter is in free floating position and gives accurate readings.

The relative height of the hydrometer is sensed by control head 8. The structure of the upper portion of the hydrometer 15 together with the control head is such as to serve to indicate the specific gravity or concentration of the liquid in chamber 5 by any of numerous conventional means. For example, photoelectric, linear transducer, or magnetic means can be used. The top portion 15 of the hydrometer may be in the form of a light reflector material which serves as a reflective flag to a light beam emanating across the control head at a given height thereof so that the point at which the light reflective portion of the hydrometer interrupts the light beam corresponds to a given reading, indicator light or the like.

In a preferred aspect of the present invention control head 8 is movable in position. Its height is set so that when the density or concentration of solution in chamber 5 is at the desired level (and accordingly the hydrometer floats at the corresponding height) the sensing system in the control head is aligned with the sensing means 15 in the hydrometer to reflect zero correction and/or that the unit is operating at the set desired conditions. Thereafter, as the concentration of the liquid in the processing unit varies, and thus the concentration of the liquid in the chamber 5 changes, the resulting change in height of the hydromer 7 relative to the set position of the movable control head will indicate a correction is necessary to the operation of the overall system. Thus, if the solution density should decrease, the hydrometer will fall and the control head would indicate by means of any of a variety of indicators 10 such as a pilot light system that the density has dropped. By suitable electronic, electromechanical or mechanical mchanisms this can in turn be used to control operations in the principal unit to restore the desired specific gravity or concentration, such as for example, by increasing the feed of syrup to a beverage system, decreasing the relative amount of water as compared to more concentrated ingredients, increasing the heat applied to the system for concentration purposes, etc. Converse corrections would be made, of course, if the concentration were to increase unduly beyond the set point, the consequent rise of the hydrometer being sensed by the control head and translated into appropriate action.

Typically, the height of the control head may be adjusted by adjustment screw system 12. In the case of making beverages or the like, a separate test measurement is made by means not shown, of the concentration, specific gravity or Brix of the liquid to be monitored. When it is at the desired conditions as determined by this measurement the height of the control head 8 is varied by means of adjustment screw 12 so as to be aligned with the height of the hydrometer 15 corresponding to that density by virtue of the solution in chamber 5, to indicate a set or no change position. Thereafter, as changes do occur in the operation of the system departures from this set position by virtue of changes in elevation of the hydrometer are in turn reflected either by an indicator system and/or corrections to the operation of the unit so as to reestablish the desired conditions. In one such system a series of warning lights corresponding to given deviations in specific gravity or Brix from the desired conditions are used. Thus, the operator by looking at the control panel pilot light which is thereby lit can determine the direction of departure from desired conditions and approximate degree of departure and thus make appropriate corrections to the operation of the processing unit. These corrections, of course, as indicated previously can be made automatic by appropriate electro or electromechanical systems, or manually.

In another aspect of the present invention a pressure pump, not shown, is used to produce a sample flow of beverage or a liquid solution to be monitored to flow through opened valve 18 and pipe 2 into chamber 1. The flow switch within the monitor actuates a 2 minute time delay. During this time period the temperature and specific gravity of the liquid in the chambers are allowed to stabilize and no readings are taken. Thereafter, the control monitor system will be actuated to monitor the condition of the liquid and give appropriate reflection thereof as described previously.

A temperature compensating mechanism may be used to sense the liquid temperature with thermowell 11 positioned in the liquid flowing in pipe 2 and to adjust the height of the control head 8 to compensate for the temperature variation effect on the hydrometer. Thus, a temperature increase would cause the control hydrometer to fall and a temperature decrease would cause the control hydrometer to rise. By moving the control head up and down with the temperature variation the effect of the liquid temperature change on the hydrometer can be negated and the control head will then sense only changes in the concentration.

A preferred embodiment for effecting temperature compensation is shown in the drawing. Finned hydrometer 7 floats in the reservoir liquid with the sensing means positioned within control head 8. The height of the control head is manually adjustable by adjustment screw 12. The height of control head 8 is further changed by means of the temperature compensator comprising thermowell 11 and bellows 21. The thermowell detects the temperature difference of the solution from standard conditions and raises or lowers the control head to balance out the temperature effect. For example, if the temperature increases, the control head is lowered a sufficient amount to compensate for dropping of the hydrometer due to the temperature effect.

Accordingly, the present invention serves as a sensitive and accurate means of continuously monitoring the concentration or density of a liquid from a processing unit by use of the multizone reservoir chamber system described and finned hydrometer rotated by the resultant liquid streams formed. Accurate readings are obtained which are not affected by variations in the flow rate of the liquid in the processing conditions as would be the case if a hydrometer or other unit were placed directly therein.

Various modifications may be made to the present invention. By way of example, it may be possible to arrange the holes in the baffle to give the hydrometer other than rotary motion and yet provide a free floating condition not affected by bubbles, etc. so as to thereby provide accurate readings.

Having described the present invention, that which is sought to be protected is set forth in the following claims.

What is claimed is:

1. An apparatus for determining the density of a liquid sample from a processing unit which comprises:
   a first chamber and a second chamber for holding liquid sample from said processing unit,
   said second chamber having a finned hydrometer adapted to freely rotate in sample liquid contained therein,
   said first chamber having a liquid overflow passage, and said second chamber having a liquid overflow passage, the overflow passage of said first chamber being at a higher elevation than that of said second chamber,
   said first chamber and said second chamber being separated by a wall having openings provided therein so as to cause liquid to flow as a plurality of lateral streams from said first chamber to said second chamber,
   means for feeding sample liquid from said processing system to said first chamber,
   the aforesaid means causing liquid to flow from said first chamber laterally into said second chamber in the form of a liquid stream entering said second chamber in the form of a liquid stream entering said second chamber at about a height corresponding to the position of the body of the finned hydrometer so as to turn said finned hydrometer, and means for sensing the relative height of said hydrometer so as to indicate the density of the sample liquid.

2. The apparatus of claim 1 which further comprises control head positioned in the upper portion of said second chamber and adapted to respond to the relative height of said finned hydrometer floating therein thereby reflecting the density of the sampled solution.

3. The conrol head of claim 2 which is vertically movable so as to be initially set in a predetermined position.

4. The apparatus of claim 3 which comprises adjustable screw means for setting the relative vertical position of said control head.

5. The apparatus of claim 2 which further comprises correction means actuated by said control head to vary conditions in said processing system in response to the height of said hydrometer.

6. The apparatus of claim 1 which further comprises control activation means responsive to the height of said hydrometer.

7. The apparatus of claim 1 wherein said liquid overflow passages take the form of a plurality of overflow holes located in the upper portions of said first and second chambers.

* * * * *